(12) United States Patent
Takase et al.

(10) Patent No.: US 7,738,934 B2
(45) Date of Patent: Jun. 15, 2010

(54) BIOLOGICAL COMPONENT MEASURING APPARATUS AND METHOD

(75) Inventors: Tomohiro Takase, Kanagawa (JP); Isao Nawata, Kanagawa (JP); Ikuo Uematsu, Kanagawa (JP); Kayoko Oomiya, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 842 days.

(21) Appl. No.: 11/538,230

(22) Filed: Oct. 3, 2006

(65) Prior Publication Data
US 2007/0219436 A1  Sep. 20, 2007

(30) Foreign Application Priority Data
Mar. 17, 2006  (JP)  ............................... 2006-074596

(51) Int. Cl.
*A61B 5/145* (2006.01)
(52) U.S. Cl. ...................................... 600/310; 600/344
(58) Field of Classification Search ................. 600/310, 600/316, 322, 344, 347, 365
See application file for complete search history.

(56) References Cited

U.S. PATENT DOCUMENTS 5,058,588 A * 10/1991 Kaestle .................... 600/323
6,771,994 B2 * 8/2004 Kiani et al. ............... 600/323
2002/0038081 A1 * 3/2002 Fein et al. .................. 600/323
2004/0162471 A1 * 8/2004 Ikeda et al. ................ 600/322

FOREIGN PATENT DOCUMENTS

| JP | 9-61346 | 3/1997 |
|---|---|---|
| JP | 2000-227 | 1/2000 |
| JP | 2002-191582 | 7/2002 |

\* cited by examiner

*Primary Examiner*—Eric F Winakur
*Assistant Examiner*—Etsub D Berhanu
(74) *Attorney, Agent, or Firm*—Oblon, Spivak, McClelland, Maier & Neustadt, L.L.P.

(57) ABSTRACT

A measuring apparatus uses a biological component sensor including a plate-shaped sensor chip having a biological component sensing function and a sensor chip holding frame surrounding and holding the sensor chip. The biological component sensor is disposed in a measuring apparatus main body housing. A fixed engaging member and movable engaging member disposed on a sensor chip support table fixed to the measuring apparatus main body housing fix and support the sensor chip holding frame, and the sensor chip can be thus replaced. The biological component sensor contacts a forearm portion of a human body, and a biological component exuded from a contact part of the forearm portion is caused to contact the sensor chip to change a physical or chemical surface property of the sensor chip, thereby measuring the change through an irradiation of an inspection light to calculate concentration of the biological component.

10 Claims, 4 Drawing Sheets

BIOLOGICAL COMPONENT MEASURING APPARATUS AND METHOD

BACKGROUND OF THE INVENTION

1. Field of the Invention

The present invention relates to a biological component measuring apparatus and method capable of measuring a biological component such as glucose without requiring means such as blood drawing.

2. Related Art

Currently, glucose measuring apparatuses of a blood drawing type have been put on the market as apparatuses for causing a patient having a glycemia to measure a blood sugar level individually. These glucose measuring apparatuses serve to draw blood from a patient by himself (herself), to drop the blood onto a glucose sensor chip, and to measure a glucose concentration based on a change in an electrical resistance value or to irradiate a light on the blood itself, thereby calculating the glucose concentration from spectral characteristics thereof. In the method, there is a great problem in that an action for drawing blood is indispensable and a slight pain is caused when drawing blood, a scar is left in a blood taking portion or excessive care is necessary for the hygiene maintenance of an injection needle to be used for drawing blood. The patients having the glycemia who are people to be measured have strongly demanded the development of a glucose measuring apparatus of a non-blood drawing type.

On the other hand, currently, a biosensor for medical research uses has been developed and practically utilized eagerly in the industrial world. In particular, there has been actively developed a technique for sticking a thin film or biological reactive material having a sensing function to a surface of a plate-shaped glass chip and causing a biological tissue or a biological tissue fluid to come in contact with this portion, thereby carrying out sensing. Moreover, there is often carried out an operation for irradiating a light on the thin film or biological reactive material having the sensing function and deciding a result of the sensing based on an optical signal which is obtained. In the sensors for the medical research uses, a sensor for measuring glucose has also been developed (see Japanese Patent Applications, Publication Nos. HEI9-61346, 2000-227, and 2002-191582). However, the measuring apparatuses using the biosensor are restricted to apparatuses for the medical research uses and installed apparatuses in hospitals. At present, there is no example in which the measuring apparatuses are practically utilized as personal and compact measuring apparatuses for the patients having the glycemia.

As sensors directed to medical research apparatuses for deciding a result of sensing by a sensor chip formed of a plate-shaped glass which has a sensing function and an optical signal obtained by irradiating a light on the sensor chip, there has been developed an apparatus having the function of causing a biological tissue to come in contact, thereby measuring a glucose. By practically utilizing the sensor as a personal and compact glucose measuring apparatus, it is possible to meet the expectations of many patients having the glycemia who desire the development of a blood sugar meter of a non-blood taking type.

SUMMARY OF THE INVENTION

In the practical utilization of the personal and compact glucose measuring apparatus, however, there are also many problems. In particular, there are the following major problems. (1) A plate-shaped glass chip to be a sensor chip which is once used is usually prevented from being recycled. Therefore, the glass chip is attached and removed every measurement. Thus, it is necessary to maintain safety and workability in the attachment and removal. (2) A person to be measured carries out an operation for the apparatus by himself (herself) while maintaining a contact of the plate-shaped glass chip and a biological tissue. Therefore, it is necessary to maintain an easiness of the operation. (3) In order to maintain precision in a light measurement, it is necessary to ensure precision in a fixing position of the plate-shaped glass chip. In the case in which the practical utilization of the compact measuring apparatus which is directed to a person to be measured is considered, the handling management of the measuring apparatus and an error detecting mechanism are very complicated. From such a background, a compact glucose measuring apparatus directed to a person to be measured which uses a plate-shaped glass sensor chip has not been practically utilized and it has been demanded to solve these problems.

A biological component measuring apparatus according to an embodiment of the present invention comprises:

a biological component sensor including a plate-shaped sensor chip having a biological component sensing function and a sensor chip holding frame surrounding and holding the sensor chip;

a measuring apparatus main body housing for mounting the biological component sensor thereon;

a fixed click-shaped engaging member fixed to the measuring apparatus main body housing; and a movable click-shaped engaging member disposed in the measuring apparatus main body housing to be movable, wherein the biological component sensor is held by the fixed click-shaped engaging member and the movable click-shaped engaging member, and the biological component sensor is caused to come in contact with a forearm portion of a human body and a concentration of a biological component exuded from a contact portion of the forearm portion is measured.

Preferably, in the biological component measuring apparatus according to the embodiment of the present invention, a contact sensor is provided in a position in which the biological component sensor is attached in the measuring apparatus main body housing.

Preferably, in the biological component measuring apparatus according to the embodiment of the present invention, a switch of a slide mechanism is used as a switch which controls a supply of a power to the biological component measuring apparatus, and a push button switch is used as a switch which operates the measuring apparatus.

Preferably, in the biological component measuring apparatus according to the embodiment of the present invention, the biological component measuring apparatus is driven by a battery, a space for accommodating the battery is provided in the measuring apparatus main body housing and a part of the measuring apparatus main body housing is taken away to form an opening for accommodating the battery, and the opening is closed and an opening/closing cover having a cylindrical projection is rotatably fitted in the opening by setting the cylindrical projection to be a rotating shaft.

Preferably, in the biological component measuring apparatus according to the embodiment of the present invention, an opening for inserting a setting information recording device and a setting information recording device connecting terminal are provided in the measuring apparatus main body housing, and the setting information recording device is inserted into the opening, thereby giving a function of switching an operation mode of the measuring apparatus or a function of identifying the sensor chip.

Preferably, in the biological component measuring apparatus according to the embodiment of the present invention, the measuring apparatus main body housing includes a lower housing to come in contact with the forearm portion of the human body and an upper housing for accommodating the biological component sensor, the upper housing and the lower housing are coupled to be rotatable by means of a rotating mechanism, and the upper housing and the lower hosing closely contact with each other, and fixed and engaged with each other, and they closely contact with the forearm portion of the human body so that the biological component sensor closely contacts with a subcutaneous tissue of the forearm portion of the human body.

Preferably, a contact sensor is provided in the upper housing or lower housing.

Preferably, in the biological component measuring apparatus according to the embodiment of the present invention, a hinge is used as the rotating mechanism and a maximum rotating angle is set to be 150° to 180°.

Preferably, the biological component measuring apparatus according to the embodiment of the present invention further comprises a push button which releases the fixation and engagement of the upper housing and the lower housing.

A biological component measuring method according to an embodiment of the present invention comprises: bringing a biological component measuring apparatus including at least a biological component sensor including a plate-shaped sensor chip having a biological component sensing function and a sensor chip holding frame surrounding and holding the sensor chip, a measuring apparatus main body housing for mounting the biological component sensor thereon, a fixed click-shaped engaging member fixed to the measuring apparatus main body housing, a movable click-shaped engaging member disposed in the measuring apparatus main body housing to be movable, the biological component sensor being held by the fixed click-shaped engaging member and the movable click-shaped engaging member, a light source disposed in the measuring apparatus main body housing and serving to irradiate an inspection light on the biological component sensor, and a photoreceptor which receives the inspection light emitted from the light source and reflected from the biological component sensor, in a close contact with a forearm portion of a human body; irradiating the inspection light from the light source; receiving the inspection light reflected from the biological component sensor through the photoreceptor; and measuring an amount of a biological component from an amount of the light.

A biological component measuring method according to an embodiment of the present invention comprises bringing a biological component measuring apparatus including at least a biological component sensor including a plate-shaped sensor chip having a biological component sensing function and a sensor chip holding frame surrounding and holding the sensor chip, a measuring apparatus main body housing for mounting the biological component sensor thereon, a fixed click-shaped engaging member fixed to the measuring apparatus main body housing, a movable click-shaped engaging member disposed in the measuring apparatus main body housing to be movable, the biological component sensor being held by the fixed click-shaped engaging member and the movable click-shaped engaging member, a light source disposed in the measuring apparatus main body housing and serving to irradiate an inspection light on the biological component sensor, and a photoreceptor which receives the inspection light emitted from the light source and reflected from the biological component sensor, in a close contact with a forearm portion of a human body, thereby measuring a biological component exuded from the forearm portion of the human body, wherein the biological component sensor is attached to the measuring apparatus main body housing and then the inspection light is irradiated, thereby deciding a type of the sensor chip or an attachment situation of the biological component sensor based on a magnitude of a signal obtained by measuring the inspection light reflected from the biological component sensor.

According to embodiments of the present invention, it is possible to easily measure the amount of a biological component such as glucose without requiring an ordinary person who is to be measured to have special knowledge and techniques.

DETAILED DESCRIPTION OF PREFERRED EMBODIMENTS

In the following description of an embodiment, the present invention is applied to glucose as a biological component. However, the present invention can be applied not only to glucose but also to other components exuded from a subcutaneous tissue of a skin of a human body.

[Principle of Measurement for Amount of Biological Component to be used in the Invention]

A principle for measuring the amount of glucose to be used in the present invention will be described below with reference to FIG. 3 which is an enlarged view showing a main part of glucose amount measuring apparatus according to embodiments of the present invention.

Figure 3:
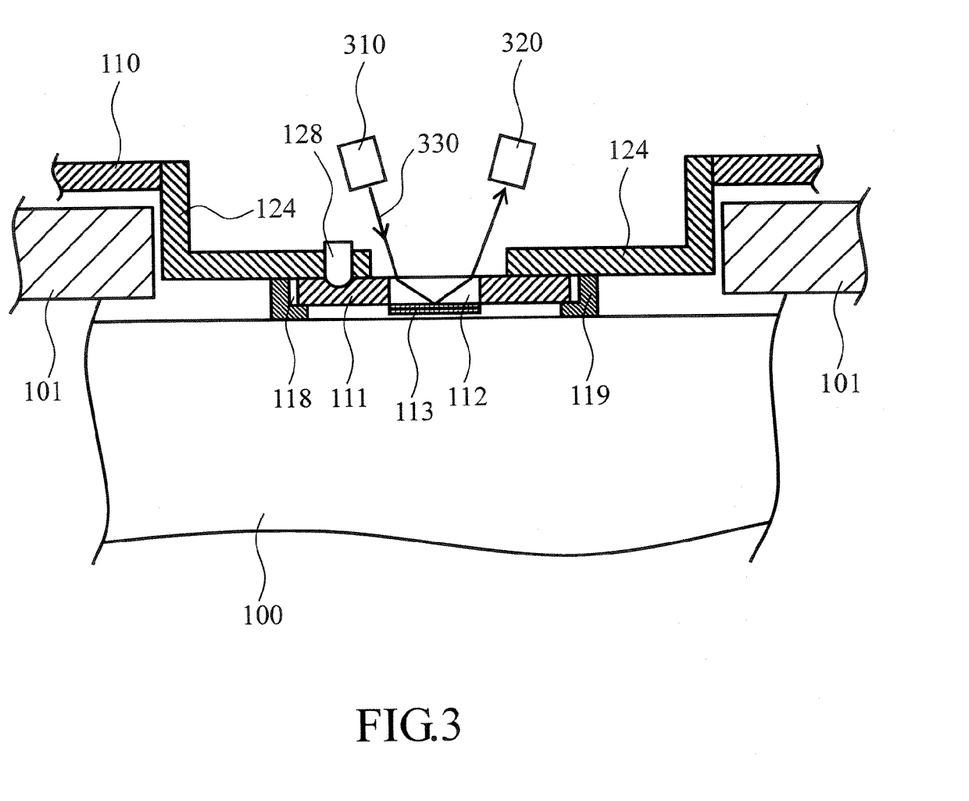
FIG. 3 is an enlarged sectional view showing a main part of the measuring apparatus in FIGS. 1A and 1B.

In FIG. 3, 100 denotes a forearm portion of a person to be measured, and a sensor chip 112 to be a sensor for measuring an amount of the glucose is provided in close contact with a surface of a skin of the forearm portion. A body fluid exuded from the surface of the skin of the person to be measured comes in contact with a sensor film 113 applied to a surface of the sensor chip 112 and causes a chemical reaction with the glucose present in the body fluid so that the properties of the surface of the sensor film 113 are changed. The amount of the change is proportional to that of the glucose in the body fluid. A coherent inspection light 330 such as a laser beam is irradiated from a light source 310 incorporated in a measuring apparatus main body 110 onto the sensor chip 112 in which the properties of the surface are changed, and is reflected by the surface of the sensor chip 112, and the amount of the light is measured by a photoreceptor 320 incorporated in the measuring apparatus main body 110. The amount of the inspection light is attenuated proportionally to the amount of the glucose. Therefore, it is possible to calculate the amount of the glucose from the amount of the light attenuation which is observed.

In the measurement, it is also possible to mechanically or electrically stimulate the surface of the skin, thereby promoting the exudation of the body fluid before causing the surface of the skin of the forearm portion of the person to be measured to come in contact with the sensor chip.

In the measuring apparatus, a change in an optical path of the inspection light greatly influences the amount of the inspection light observed by the photoreceptor. Consequently, the great influence sensitively results in an error of the measurement of the glucose concentration. Even if an ordinary person to be measured operates the measuring apparatus according to the present invention, accordingly, it is necessary to prevent a great change from being caused over the optical path for the inspection light. The embodiment of the measuring apparatus according to the present invention which will be described below is intended for the realization of a measuring apparatus having a high operability and reliability which can prevent precision in an inspection from being easily deteriorated when the ordinary person to be measured uses the measuring apparatus.

EMBODIMENT OF MEASURING APPARATUS

Figure 1A:
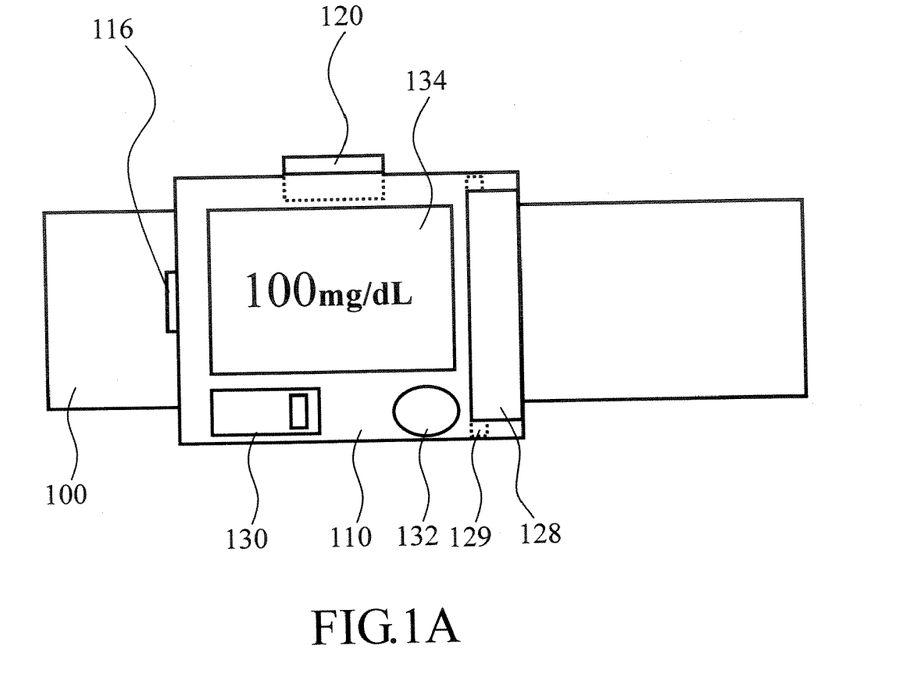
FIGS. 1A and 1B are top and side views showing a measuring apparatus according to an embodiment of the present invention.
Figure 1B:
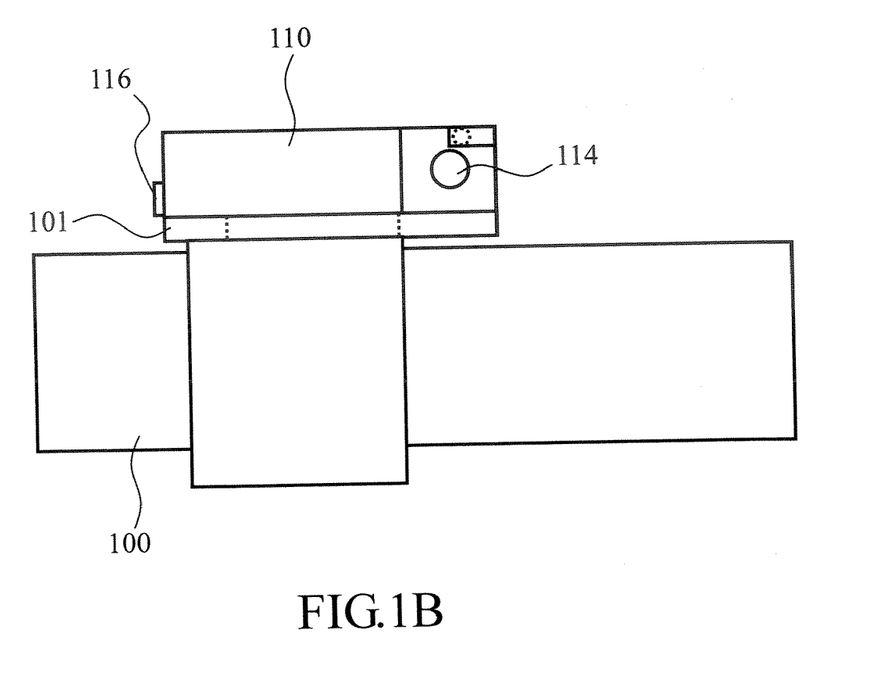
Figure 2A:
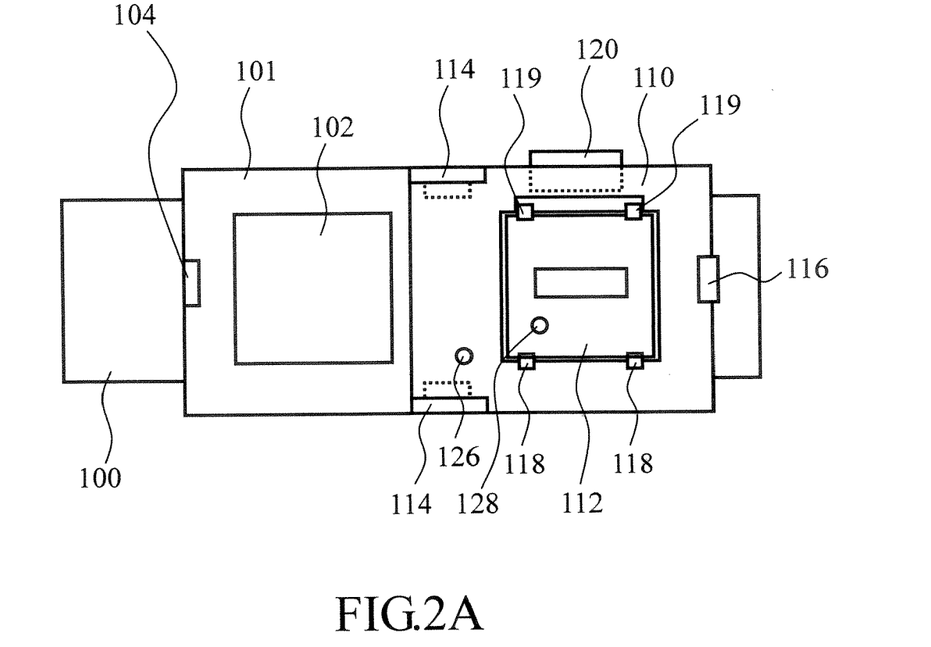
FIGS. 2A and 2B are top and side views showing a state in which the measuring apparatus in FIGS. 1A and 1B is opened.
Figure 2B:
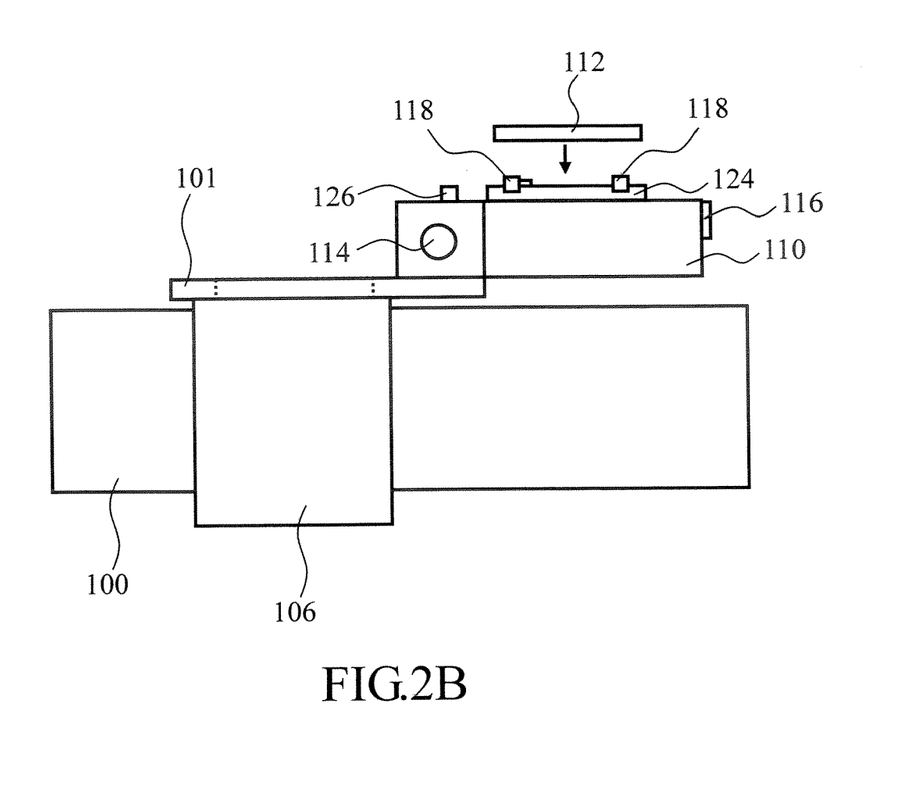

An embodiment of a glucose measuring apparatus according to the present invention will be described below with reference to FIGS. 1A to 3. FIGS. 1A and 1B are views showing a state in which the glucose measuring apparatus according to the present invention is used, and FIG. 1A is a front view showing the glucose measuring apparatus and FIG. 1B is a side view showing the same. Moreover, FIGS. 2A and 2B are views showing a state in which a receiving table 101 and the measuring apparatus main body 110 in the glucose measuring apparatus of FIG. 1 are opened, and FIG. 2A is a front view showing the same and FIG. 2B is a side view. Furthermore, FIG. 3 is an enlarged sectional view showing the main part of the glucose measuring apparatus as described above.

In FIG. 1, the glucose measuring apparatus comprises the receiving table 101 which comes in close contact with the forearm portion of a person to be measured and the measuring apparatus main body 110 coupled to the receiving table 101. They are coupled to be rotatable by a rotating mechanism 114 such as a hinge. The receiving table 101 and the measuring apparatus main body 110 can fix the glucose measuring apparatus to a forearm portion 100 of the person to be measured by means of a belt 106 coupled to the receiving table 101, thereby carrying out the measurement.

It is preferable that the rotating mechanism 114 be set to have a maximum rotating angle of 150° to 180°. In the case in which the maximum rotating angle is smaller than the range, an angle formed by the receiving table 101 and the measuring apparatus main body 110 is so small that a work for replacing the sensor chip 112 or the like is hindered. On the other hand, the maximum angle of 180° or more is not preferable because a part of the measuring apparatus main body 110 comes in contact with the forearm portion of the person to be measured to cause instability when the measuring apparatus main body is opened.

As shown in FIG. 1, the outer surface of the measuring apparatus main body 110 in a closing state is provided with a display device 134, a power switch 130 and a push button switch 132 to be an operating switch. The display device 134 can display a result of the measurement obtained by the measuring apparatus, an operating situation of the measuring apparatus, an error message given in case of a malfunction or information about the description of the use of the apparatus. Moreover, the power switch 130 supplies and cuts off a power from a battery incorporated in the apparatus. For the switch, a slide switch is preferably used in order to prevent the malfunction. Moreover, the operating switch 132 such as a push button switch is used for carrying out various operations and can be used as a start key for different operations corresponding to an operation mode of the measuring apparatus. More specifically, the operating switch 132 can also be used as a start key for starting the measurement, a setting key in a step for setting the measuring apparatus, a reset switch for initializing various settings or the like. For the switch, the push button switch is preferably used because of the easiness of an operation.

During the use of the measuring apparatus, as shown in FIG. 1B, the receiving table 101 and the measuring apparatus main body 110 are engaged with each other through engaging tool 104 so that the measuring apparatus main body 110 can be prevented from being opened carelessly. The engagement of the engaging tool 104 is released through a main body disengaging button 116 and the measuring apparatus main body 110 is rotated around the rotating mechanism 114 so that the receiving table 101 and the measuring apparatus main body 110 are opened.

Description will be given with reference to FIGS. 2A and 2B showing a state in which the receiving table 101 and the measuring apparatus main body 110 are opened. As shown in FIG. 2A, the receiving table 101 has a window portion 102 formed in a central part. In the case in which the measuring apparatus is attached to the forearm portion of the person to be measured and the apparatus main body 110 is opened, the surface of the skin of the forearm portion is exposed through the window portion 102. The engaging tool 104 is disposed on an end of the receiving table 101 on the opposite side of an end of the receiving table 101 where the rotating mechanism 114 is provided, and serves to engage the receiving table 101 to the measuring apparatus main body 110 in cooperation with an engaging tool 116 of the measuring apparatus main body 110 as described above.

The main part of the measuring apparatus according to the present embodiment will be described with reference to FIG. 3 which is the enlarged sectional view showing the main part of the measuring apparatus according to the present embodiment.

A sensor chip support table 124 is disposed on a surface at an inside of the measuring apparatus main body 110. A pair of fixed click-shaped engaging members 118 and a pair of movable click-shaped engaging members 119 are disposed in contact with the sensor chip support table 124. A sensor chip holding frame 111 mounting the sensor chip 112 thereon is mounted on the sensor chip support table 124. The sensor chip holding frame 111 is mounted on the sensor chip support table 124 and is fixed onto the sensor chip support table 124 through the fixed click-shaped engaging members 118 and the movable click-shaped engaging members 119. The fixed click-shaped engaging member 118 is fixed to the measuring apparatus main body 110, while the movable click-shaped engaging member 119 is movable in such a direction as to approach and separate from the fixed click-shaped engaging member 118 (a transverse direction in FIG. 3). The movable click-shaped engaging member 119 is always biased in a leftward direction of the drawing through a biasing member such as a spring which is not shown, and serves to fix the sensor chip holding frame 111 in cooperation with the fixed click-shaped engaging member 118. When removing the sensor chip holding frame 111 from the measuring apparatus main body 110, the movable click-shaped engaging member 119 is forcibly moved in a rightward direction of FIG. 3 to disengage the sensor chip holding frame 111.

The sensor chip 112 is formed of a thin glass plate. If a person directly handles the sensor chip 112, there is a great possibility that he (she) might be injured. For this reason, it is preferable that the sensor chip holding frame 111 be formed of plastic.

As shown in FIG. 2, a receiving table detecting contact switch 126 is disposed on a surface at an inside of the measuring apparatus main body 110. The receiving table detecting contact switch 126 is disposed on the surface of the measuring apparatus main body 110 and serves to detect that the measuring apparatus main body 110 and the receiving table 101 have come in contact with each other, and are thus engaged with each other and are integrated. The information about the detection is input to a control device of the measuring apparatus and is used for controlling a measuring process.

In the glucose measuring apparatus according to the present embodiment, it is necessary to confirm the engagement and integration of the measuring apparatus main body 110 and the receiving table 101 in order to decide whether the preparation for measurement is normally done or not. For this purpose, it is possible to detect the integration of the measuring apparatus main body 110 and the receiving table 101 and to appropriately grasp the progress of a preparation by means of the receiving table detecting contact switch 126.

The receiving table detecting contact switch may be disposed as a switch for detecting the measuring apparatus main body on the receiving table side.

As shown in FIG. 3, moreover, a sensor chip detecting contact switch 128 is disposed on the surface of the sensor chip support table 124 and serves to detect whether the sensor chip holding frame 111 is normally mounted on the sensor chip support table 124 or not. The information about the detection is input to the control device of the measuring apparatus and is used for controlling the measuring process.

In the glucose measuring apparatus according to the present embodiment, it is necessary to confirm whether the sensor chip frame is normally attached or not in order to decide whether the preparation for measurement is normally done or not. For this purpose, it is possible to detect the state of an attachment, thereby grasping the progress of the preparation appropriately by means of the sensor chip detecting contact switch 128.

It is preferable that the glucose measuring apparatus according to the present embodiment be driven by means of an AA size battery or an AAA size battery. A battery housing portion of the measuring apparatus according to the present embodiment will be described with reference to FIG. 4 which is a perspective view showing a main part and FIG. 5 which is a side view showing a cover of the battery housing portion.

Figure 4:
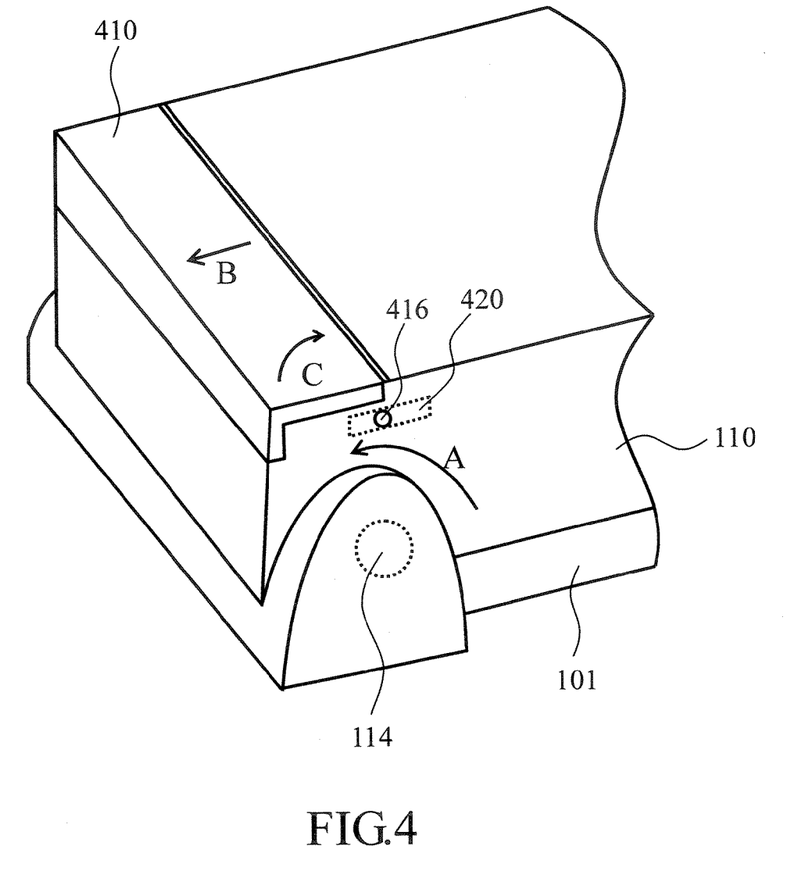
FIG. 4 is a perspective view showing a part of the vicinity of a battery housing of the measuring apparatus in FIGS. 1A and 1B.

A space for accommodating a battery to be a power supply for driving the measuring apparatus is provided close to the rotating mechanism 114 of the measuring apparatus main body 110, and a battery cover 410 covers the battery housing portion. The battery cover 410 includes a battery cover main body 410 and a rotating shaft 416 fixed and disposed onto a lower part of the battery cover main body 410. A guide groove 420 capable of fitting the rotating shaft 416 therein is formed on the inside of the measuring apparatus main body as shown in FIG. 4, and the battery cover body 410 is coupled to the measuring apparatus main body 110 by fitting of the rotating shaft 416 in the guide groove 420. Moreover, the guide groove 420 is formed in parallel with the upper surface of the measuring apparatus main body 110 and the battery cover body 410 can be moved in a direction of an arrow B in FIG. 4. The battery cover body 410 is rotated in a direction of an arrow C in FIG. 5 around the rotating shaft 416 in a position pulled out in such a separating direction from the measuring apparatus main body 110 and a battery for driving the measuring apparatus can be accommodated in and taken out of the measuring apparatus main body.

Figure 5:
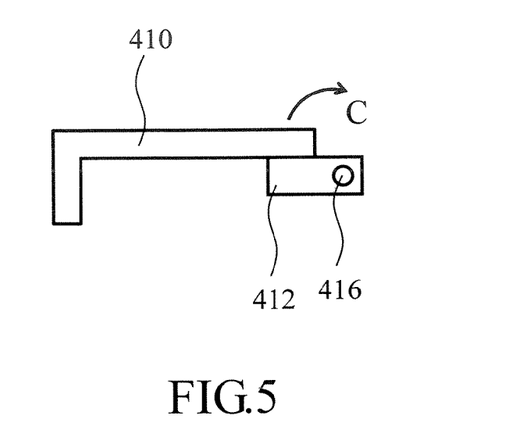
FIG. 5 is a side view showing a battery cover illustrated in FIG. 4.

With such a structure of the battery cover, it is possible to prevent the battery cover 410 from carelessly separating and slipping when the battery is replaced. Moreover, the battery cover can also be assembled easily.

As shown in FIG. 1, an inserting port for an information card to be a recording device for setting the measuring apparatus is disposed on the measuring apparatus main body 110 and an information card 120 is inserted in the inserting port to input information for setting the operation of the glucose measuring apparatus or specifying the type of the sensor chip, and the information can be input to the glucose measuring apparatus. A plurality of terminals for transmitting the recorded information is formed on the information card. On the other hand, the inserting port is provided with a connector for a connection to the terminals. The information card may be a card mounting a semiconductor device recording setting information or the like on a substrate or a card which has a plurality of terminals provided on the substrate and a power line terminal and in which a specific one of the terminals is connected to the power line terminal and information is recorded by a combination of terminal positions in which a power line is connected. More specifically, the information card has six terminals and one power line terminal and they are connected to each other in the card so that 64 setting states can be indicated.

By using this structure, it is possible to switch the operation mode of the measuring apparatus and to recognize the type of a chip without carrying out a complicated operation.

As shown in FIG. 3, the sensor chip 112 is mounted on the sensor chip holding frame 111, and the surface of the sensor film 113 of the sensor chip 112 is exposed from the surface of the body in a state in which the measuring apparatus main body 110 is opened from the receiving table 101. A chip attachment surface of the measuring apparatus main body 110 is stationary in a state in which an angle of 150° to 180° is formed with respect to the skin tissue surface of a forearm skin portion. Therefore, it is possible to attach and remove the chip without removing the measuring apparatus itself from the forearm.

In a state in which the measuring apparatus main body is closed to engage and integrate the measuring apparatus main body 110 and the receiving table 101, the sensor chip holding frame 111 can be fitted in the window portion 102 of the receiving table 101 and can closely contact the skin surface of the forearm portion of the human body.

It is preferable that the sensor chip holding frame 111 be formed by a resin. By doing so, the person to be measured does not directly touch the sensor chip which is usually formed by a glass plate member. Therefore, it is possible to prevent an accident such as an injury from being caused by handling of the glass chip.

As shown in FIG. 3, the measuring apparatus main body 110 includes the light source 310, the photoreceptor 320 for receiving the inspection light 330 emitted from the light source 310 and reflected from the sensor chip 112, and a control device for controlling them (not shown).

The battery, the power switch 130, the operating switch 132, the receiving table contact switch 126, the sensor chip contact switch 128, the display device 134, an information card connector, the light source 310, the photoreceptor 320 and the like are electrically connected to the control device and the operation of the measuring apparatus is thus controlled.

The sensor chip 112 has such a structure that the sensor film 113 is formed on the surface of the substrate such as a translucent glass, and the sensor chip 112 is fixed to the sensor chip holding frame 111 as shown in FIG. 3.

[Glucose Measuring Method]

By using the glucose measuring apparatus, it is possible to analyze the amount of the glucose contained in a material exuded from the forearm portion of the human body to be a specimen by the following method.

As shown in FIG. 1, first of all, the glucose measuring apparatus is fixed to the forearm portion 100 of a subject by using the fixing tool 106 such as a belt. The measuring apparatus main body 110 is opened from the receiving table 101 and the sensor chip 112 is disposed on the sensor chip support table 124 to move the movable click-shaped engaging member 119, thereby fixing the sensor chip 112 onto the sensor chip support table 124 in cooperation with the fixed click-shaped engaging member 118.

Next, the measuring apparatus main body 110 is rotated around the rotating mechanism 114 and is thus caused to come in close contact with the receiving table 101. In this state, the sensor chip 112 is fitted in the window portion 102 of the receiving table 101 so that the surface of the sensor chip 112 comes in close contact with the surface of the forearm portion skin 100 of the person to be measured.

Then, the power switch 130 is turned on to start the glucose measuring apparatus, and the information card 120 is inserted into the inserting port to set measuring conditions, thereby causing the glucose measuring apparatus to start up if necessary.

When the glucose measuring apparatus has started up and a preparation for the measurement is completed, the operating switch 132 is pushed to start the measurement.

By pushing the operating switch 132, the control device of the glucose measuring apparatus starts the measurement by the following operation. First of all, if the information card 120 has been inserted, the setting information of the information card 120 is read to set the operation mode. Next, the light source 310 is turned on to irradiate a coherent inspection light such as a laser beam on the sensor chip 120. A body fluid exuded from the skin of the forearm portion of the person to be measured is stuck to the surface of the sensor chip to change the properties of the surface of the sensor chip by an interaction such as a chemical reaction. The change is proportional to the concentration of the glucose contained in the body fluid or the like. The light reflected by the surface of the sensor chip is attenuated proportionally to the concentration of the glucose. Therefore, the amount of the reflected light is measured by the photoreceptor incorporated in the body 110 and is converted into the concentration of the glucose. The concentration of the glucose thus obtained is displayed by the display device 134.

The measurement of the glucose is carried out in a state in which the rotating angle of the measuring apparatus main body is 0°, that is, the measuring apparatus main body and the receiving table are engaged and integrated with each other and the chip attached to the measuring apparatus main body closely contacts with the skin tissue surface of the forearm portion. A time required for the measurement is several seconds to several tens seconds. When the measuring apparatus main body and the receiving table are carelessly disengaged from each other and the measuring apparatus main body is moved around the rotating mechanism 114 during this time, it is impossible to obtain an accurate result of the measurement. By providing an engaging mechanism for locking the integration when engaging and integrating the measuring apparatus main body 110 and the receiving table 101, therefore, it is possible to considerably reduce a generation frequency of measuring errors.

According to the glucose measuring apparatus, the amount of the glucose contained in the body fluid can be measured without depending on means such as blood drawing and damaging the human body, and ordinary consumers can measure a blood sugar level on a daily basis.

[Variant]

In the glucose amount measuring method, it is possible to give the function of irradiating a sensing light on a sensor chip before carrying out a glucose measurement after attaching the sensor chip and deciding the type of the chip and quality of a chip attachment based on a magnitude of a measuring signal. By passing through the process before the start of the measurement, it is possible to considerably enhance the reliability of a result of the measurement.

As described above, moreover, it is possible to promote the exudation of a subcutaneous-tissue-containing material by electrically or mechanically pretreating the measuring part of the forearm portion before carrying out the glucose measurement. In order to carry out the electrical treatment, a chip for an electrical treatment is attached to the measuring apparatus main body in place of the glucose sensor chip. In this case, however, two types of chips, that is, the pretreating chip and the glucose sensor chip are attached to the main body portion of the measuring apparatus at different steps. In the case in which the person to be measured attaches an erroneous chip, the sensing light can be irradiated on the sensor chip to decide the type of the chip and the quality of the chip attachment based on the magnitude of the measuring signal after confirming the attachment of the sensor chip frame in order to detect the attachment. By doing so, it is possible to generate an error and an alarm to the person to be measured before starting the glucose measurement.

While the above description has been given to the example in which the glucose is selected as an object to be measured, it is also possible to apply the present invention to a biological component contained in a subcutaneous tissue other than the glucose by changing the sensor film of the sensor chip.

According to the embodiment of the present invention described above, the person to be measured can carry out a measurement preparatory work with the measuring apparatus fixed to the forearm portion. Moreover, it is possible to handle the sensor chip (frame portion) with one of hands on the opposite side of an arm to which the measuring apparatus is fixed and to easily attach the sensor chip to the main body portion of the measuring apparatus. Furthermore, a removal can easily be carried out with one hand.

According to embodiments of the present invention, thus, it is possible to implement a compact glucose measuring apparatus directed to a person to be measured. In the glucose measuring system, the plate-shaped glass sensor chip is used so that blood drawing is not required. Thus, it is possible to practically utilize a non-blood drawing type blood sugar meter expected by a large number of patients having a glycemia.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biological component measuring apparatus comprising:
   a biological component sensor including a plate-shaped sensor chip having a biological component sensing function and a sensor chip holding frame surrounding and holding the sensor chip;
   a measuring apparatus main body housing for mounting the biological component sensor thereon and including:
   a light source to irradiate light to said sensor chip, and
   a light receiving element for receive light output from internal of said sensor chip;
   a fixed engaging member fixed to the measuring apparatus main body housing; and
   a movable engaging member disposed in the measuring apparatus main body housing to be movable,
   wherein the biological component sensor is held by the fixed engaging member and the movable engaging member, and
   the biological component sensor is configured to come in contact with a forearm portion of a human body and a concentration of a biological component exuded from a contact portion of the forearm portion is measured by an amount of light detected by the light receiving element.

2. The biological component measuring apparatus according to claim 1, wherein a contact sensor is provided in a position in which the biological component sensor is attached in the measuring apparatus main body housing.

3. The biological component measuring apparatus according to claim 1, wherein a switch of a slide mechanism is used as a switch which controls a supply of a power to the biological component measuring apparatus, and a push button switch is used as a switch which operates the measuring apparatus.

4. The biological component measuring apparatus according to claim 1, wherein the biological component measuring apparatus is driven by a battery,
   a space for accommodating the battery is provided in the measuring apparatus main body housing and a part of the measuring apparatus main body housing is taken away to form an opening for accommodating the battery, and
   the opening is closed and an opening/closing cover having a cylindrical projection is rotatably fitted in the opening by setting the cylindrical projection to be a rotating shaft.

5. The biological component measuring apparatus according to claim 1, wherein an opening for inserting a setting information recording device and a setting information recording device connecting terminal are provided in the measuring apparatus main body housing, and the setting information recording device is inserted into the opening, thereby giving a function of switching an operation mode of the measuring apparatus or a function of identifying the sensor chip.

6. The biological component measuring apparatus according to claim 1, wherein the measuring apparatus main body housing includes a lower housing to come in contact with the forearm portion of the human body and an upper housing for accommodating the biological component sensor,
   the upper housing and the lower housing are coupled to be rotatable by a rotating mechanism, and
   the upper housing and the lower housing closely contact with each other, and fixed and engaged with each other, and they closely contact with the forearm portion of the human body so that the biological component sensor closely contacts with a subcutaneous tissue of the forearm portion of the human body.

7. The biological component measuring apparatus according to claim 6, wherein a hinge is used as the rotating mechanism and a maximum rotating angle is set to be 150° to 180°.

8. The biological component measuring apparatus according to claim 6, further comprising a push button which releases the fixation and engagement of the upper housing and the lower housing.

9. A biological component measuring method comprising:
   bringing a biological component measuring apparatus including at least a biological component sensor including a plate-shaped sensor chip having a biological component sensing function and a sensor chip holding frame surrounding and holding the sensor chip, a measuring apparatus main body housing for mounting the biological component sensor thereon, a fixed engaging member fixed to the measuring apparatus main body housing, a movable engaging member disposed in the measuring apparatus main body housing to be movable, the biological component sensor being held by the fixed engaging member and the movable engaging member, a light source disposed in the measuring apparatus main body housing and serving to irradiate an inspection light on the biological component sensor, and a photoreceptor which receives the inspection light emitted from the light source and reflected from the biological component sensor, in a close contact with a forearm portion of a human body;
   irradiating the inspection light from the light source;
   receiving the inspection light reflected from the biological component sensor through the photoreceptor; and
   measuring an amount of a biological component from an amount of the light.

10. A biological component measuring method comprising:
   bringing a biological component measuring apparatus including at least a biological component sensor including a plate-shaped sensor chip having a biological component sensing function and a sensor chip holding frame surrounding and holding the sensor chip, a measuring apparatus main body housing for mounting the biological component sensor thereon, a fixed engaging member fixed to the measuring apparatus main body housing, a movable engaging member disposed in the measuring apparatus main body housing to be movable, the biological component sensor being held by the fixed engaging member and the movable engaging member, a light source disposed in the measuring apparatus main body housing and serving to irradiate an inspection light on the biological component sensor, and a photoreceptor which receives the inspection light emitted from the light source and reflected from the biological component sensor, in a close contact with a forearm portion of a human body, thereby measuring a biological component exuded from the forearm portion of the human body; wherein
   the biological component sensor is attached to the measuring apparatus main body housing and then the inspection light is irradiated, thereby deciding a type of the sensor chip or an attachment situation of the biological component sensor based on a magnitude of a signal obtained by measuring the inspection light reflected from the biological component sensor.

* * * * *